(12) United States Patent
Hsieh et al.

(10) Patent No.: US 11,376,366 B2
(45) Date of Patent: Jul. 5, 2022

(54) SYRINGE APPARATUS FOR STIRRING AND DELIVERING COMPOSITION CONTAINING CELLS

(71) Applicants: Academia Sinica, Taipei (TW); Plastics Industry Development Center, Taichung (TW)

(72) Inventors: Ching-Ho Hsieh, Taipei (TW); Kuang-Ying Hsueh, Taichung (TW); Tsung-Hsuen Wu, Taipei (TW); Wen-Lin Lin, Taichung (TW); Ting-Chun Yu, Taoyuan (TW); Jin-He Ke, Taichung (TW); Li-Lun Chen, Taipei (TW); Meng-Heng Lai, Taichung (TW)

(*) Notice: Subject to any disclaimer, the term of this patent is extended or adjusted under 35 U.S.C. 154(b) by 475 days.

(21) Appl. No.: 16/078,865

(22) PCT Filed: Feb. 24, 2017

(86) PCT No.: PCT/US2017/019328
§ 371 (c)(1),
(2) Date: Aug. 22, 2018

(87) PCT Pub. No.: WO2017/147404
PCT Pub. Date: Aug. 31, 2017

(65) Prior Publication Data
US 2019/0054243 A1    Feb. 21, 2019

Related U.S. Application Data

(60) Provisional application No. 62/299,680, filed on Feb. 25, 2016.

(51) Int. Cl.
*A61M 5/178* (2006.01)
*A61M 5/31* (2006.01)
(Continued)

(52) U.S. Cl.
CPC .......... *A61M 5/3134* (2013.01); *A61M 5/178* (2013.01); *A61M 5/3135* (2013.01);
(Continued)

(58) Field of Classification Search
CPC .. A61M 5/3134; A61M 5/178; A61M 5/3135; A61M 5/31505; A61M 5/2033;
(Continued)

(56) References Cited

U.S. PATENT DOCUMENTS 3,009,686 A * 11/1961 Kaplan ................ A47J 43/105
366/276
5,665,066 A    9/1997 Fischer
(Continued)

FOREIGN PATENT DOCUMENTS

WO    2010053570 A1    5/2010
WO    2013086167 A1    6/2013

OTHER PUBLICATIONS

International Search Report Issued in Connection with Corresponding PCT Application No. PCT/US2017/019328 dated Jun. 7, 2018.

*Primary Examiner* — Nathan R Price
*Assistant Examiner* — Tania Ismail
(74) *Attorney, Agent, or Firm* — Behmke Innovation Group LLC; James M. Behmke; Jonathon P. Western

(57) ABSTRACT

A syringe apparatus is provided for stirring and delivering single or multi-component compositions. The syringe apparatus comprises a syringe barrel, a plunger, a stirring paddle, and a connecting member. The plunger partially disposed within the syringe barrel is movable along an axial direction of the syringe barrel. The stirring paddle disposed within the syringe barrel has one end passing through the plunger and slidably disposed within the plunger. The syringe apparatus of the disclosure can stir the components and deliver the
(Continued)

mixture safely for maintaining a good hygiene condition during the therapeutic process.

16 Claims, 15 Drawing Sheets

(51) Int. Cl.
    *A61M 5/315*     (2006.01)
    *A61M 5/20*     (2006.01)
    *A61M 5/28*     (2006.01)
    *A61M 5/24*     (2006.01)
    *A61M 5/46*     (2006.01)
    *A61M 5/32*     (2006.01)

(52) U.S. Cl.
CPC ....... *A61M 5/31505* (2013.01); *A61M 5/2033* (2013.01); *A61M 5/2066* (2013.01); *A61M 5/2448* (2013.01); *A61M 5/284* (2013.01); *A61M 5/31511* (2013.01); *A61M 5/31515* (2013.01); *A61M 5/31576* (2013.01); *A61M 5/3294* (2013.01); *A61M 5/46* (2013.01); *A61M 2005/2026* (2013.01); *A61M 2005/3126* (2013.01); *A61M 2005/31598* (2013.01); *A61M 2206/20* (2013.01)

(58) Field of Classification Search
CPC .... A61M 5/46; A61M 5/3294; A61M 5/2066; A61M 5/2448; A61M 5/284; A61M 5/31596; A61M 2005/31598; A61M 5/31511; A61M 5/31515; A61M 5/31576
See application file for complete search history.

(56) References Cited

U.S. PATENT DOCUMENTS

| | | | |
|---|---|---|---|
| 5,842,785 A | 12/1998 | Brown et al. | |
| 6,309,372 B1* | 10/2001 | Fischer | A61C 9/0026 433/90 |
| 9,597,454 B2* | 3/2017 | Wetzel | A61M 5/31501 |
| 2010/0174162 A1 | 7/2010 | Gough et al. | |
| 2011/0251587 A1* | 10/2011 | Banik | A61M 5/46 604/506 |
| 2014/0142507 A1 | 5/2014 | Armes | |
| 2017/0028137 A1* | 2/2017 | Mirabito | A61B 18/203 |
| 2018/0221563 A1* | 8/2018 | Frederiksen | A61M 5/3155 |

* cited by examiner

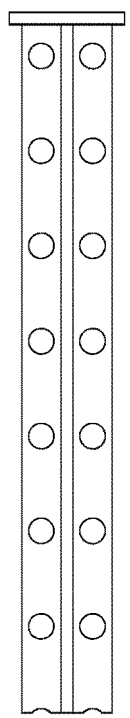 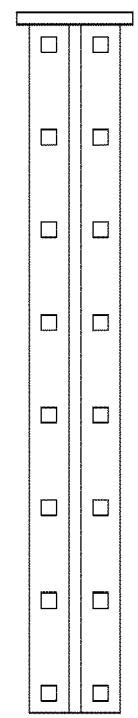
FIG. 6A  FIG. 6B
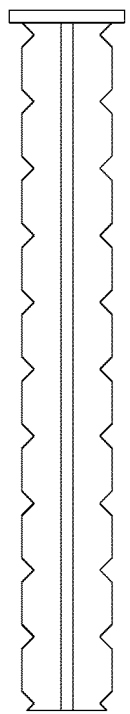 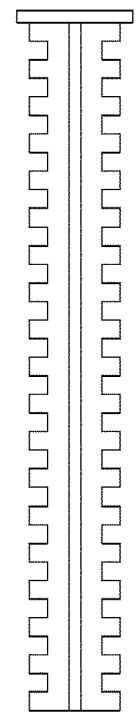
FIG. 7A  FIG. 7B

SYRINGE APPARATUS FOR STIRRING AND DELIVERING COMPOSITION CONTAINING CELLS

CLAIM FOR PRIORITY

This application is a U.S. National Phase under 35 U.S.C. 371 of International Patent Application No. PCT/US/2017/019328, filed Feb. 24, 2017, which claims the priority of U.S. Provisional Application No. 62/299,680, filed Feb. 25, 2016, the entire contents of which are incorporated herein by reference in their entirety.

RELATED APPLICATION

This application claims priority to U.S. Provisional Application No. 62/299,680 filed Feb. 25, 2016, entitled: SYRINGE APPARATUS FOR STIRRING AND DELIVERING SINGLE OR MULTI-COMPONENT COMPOSITION, by Hseih et al., the contents of which are herein incorporated by reference.

BACKGROUND OF THE DISCLOSURE

1. Field of the Disclosure

The present disclosure relates to syringe apparatuses for delivering a composition, and more particularly, to syringe apparatuses for stirring and delivering a composition containing cells.

2. Description of Related Art

In clinics, hospitals, healthcare centers and research institutions, a syringe has been the most commonly used device for injection or specimen sampling. Particularly for medical professionals, syringes that inject or extract fluids from patients play a crucial part in prevention and treatment of diseases.

Nowadays, syringes of different types and purposes have been developed according to the demand trend on the market. For example, single-use/disposable syringes, safety syringes, etc. are all now available on the market, providing the medical professionals with more choices regarding a specific medical need. Those syringes are designed with the users' concern in mind, and are more cost-effective and affordable for the public, aiming for providing a safer medical environment.

In the aspect of biotechnology, cell therapy research has been introduced in the medial field for finding effective treatments for diseases. The cell therapy unavoidably involves providing the required component(s) in a specific part with precision, which most of the time is performed by syringes during the process. However, there is no syringe specifically designed for a mixture containing cells in cell therapy so far on the market. In addition, when it comes to the use of the mixture of different components as the treatment, the syringe which can stir the components and deliver the mixture safely for maintaining a good hygiene condition during the therapeutic process remains to be seen.

SUMMARY OF THE DISCLOSURE

In view of the above-described drawbacks, the present disclosure provides a syringe apparatus for stirring and delivering a single or multi-component composition. The syringe apparatus comprises: a syringe barrel having an axial direction; a plunger detachably disposed within the syringe barrel and being movable within the syringe barrel along the axial direction of the syringe barrel, the plunger having a plunger body received in the syringe barrel and an end panel disposed at a proximal end of the plunger and protruding from the syringe barrel; a stirring paddle detachably disposed within the plunger body with the plunger being movable relative to the stirring paddle along the axial direction; and a connecting member detachably disposed within the plunger body and detachably connected between a proximal end of the stirring paddle and the end panel of the plunger.

BRIEF DESCRIPTION OF DRAWINGS

FIGS. 6A and 6B show the stirring paddle having through holes of different shapes;

FIGS. 7A and 7B show the stirring paddle having different chipping edges;

FIG. 10A' is a perspective view of another embodiment of the protection cap in FIG. 8A;

DETAILED DESCRIPTION OF EMBODIMENTS

The following illustrative embodiments are provided to illustrate the disclosure of the present disclosure. These and other advantages and effects can be apparent to those in the art after reading this specification.

It should be noted that all the drawings are not intended to limit the present disclosure. Various modifications and variations can be made without departing from the spirit of the present disclosure. Further, terms such as "first," "second," "on," "a," etc. are merely for illustrative purposes and should not be construed to limit the scope of the present disclosure.

Figure 1A:
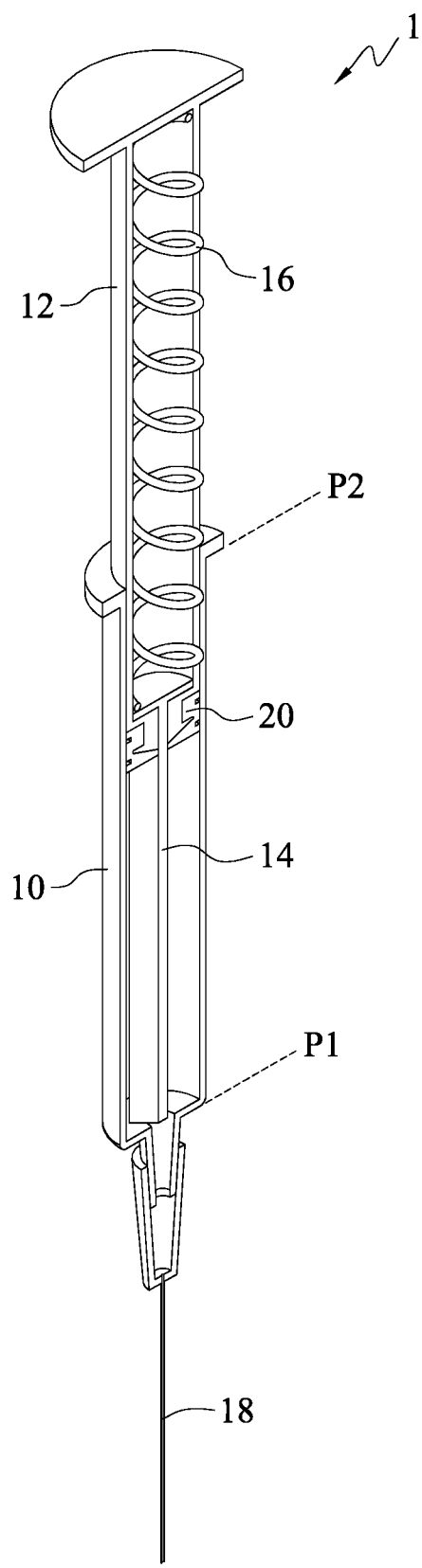
FIG. 1A is a cross-sectional perspective view of a syringe apparatus for stirring and delivering single or multi-component composition according to an embodiment of the present disclosure.
Figure 1B:
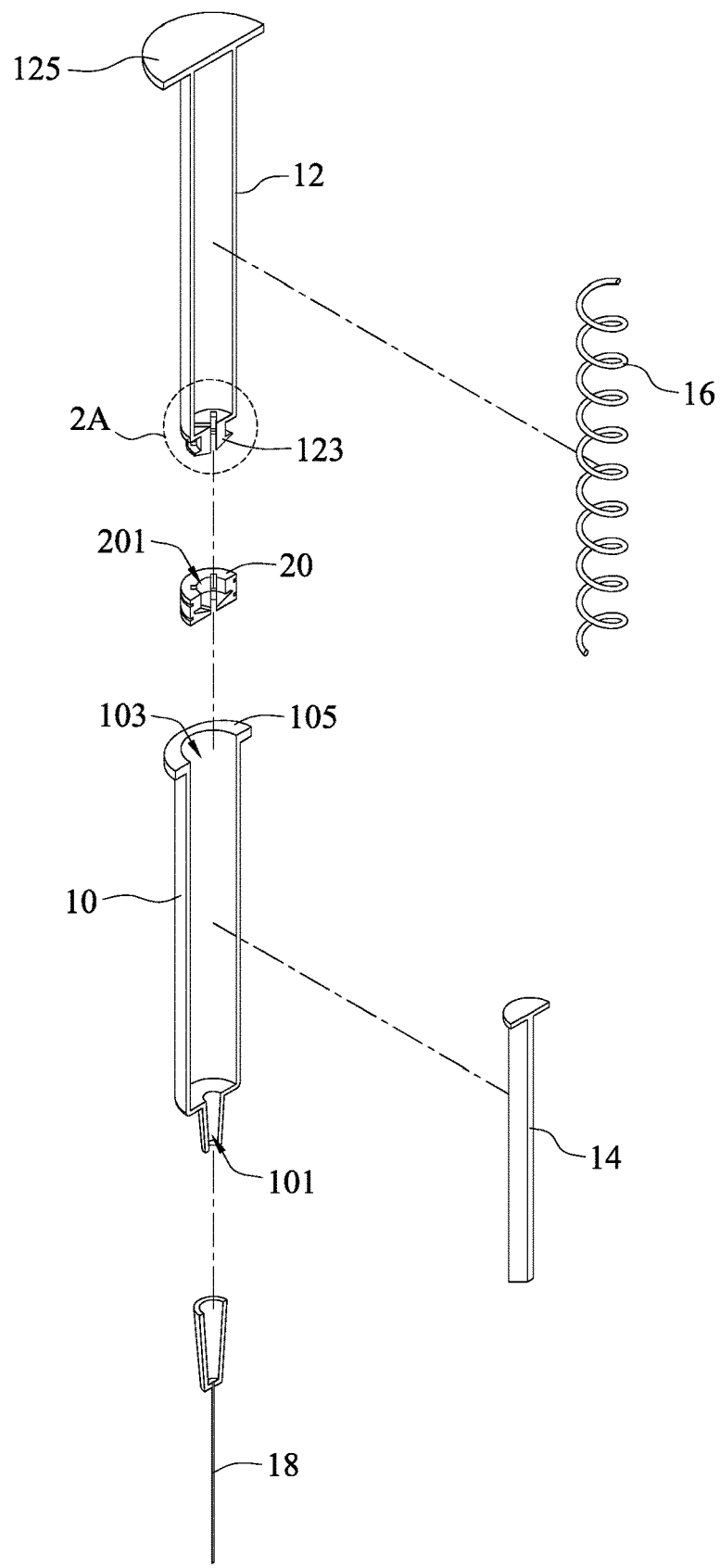
FIG. 1B is an exploded perspective view of the syringe apparatus in FIG. 1A.

FIG. 1A is a cross-sectional perspective view of a syringe apparatus 1 for stirring and delivering a composition according to an embodiment of the present disclosure. FIG. 1B is an exploded perspective view of the syringe apparatus 1 in FIG. 1A.

As shown in FIG. 1A, the syringe apparatus 1 includes a syringe barrel 10, a plunger 12, a stirring paddle 14, and a connecting member 16. For example, the connecting member 16 can be a compression spring 16. The plunger 12 is partially disposed within the syringe barrel 10 and is movable along an axial direction of the syringe barrel 10 between a contracted position P1 and a released position P2. The stirring paddle 14 is disposed within the syringe barrel 10 and has one end passing through the plunger 12 and slidably disposed within the plunger 12. The compression spring 16 is disposed within the plunger 12 and has one end leaning against the stirring paddle 14 and the other end fixed within the plunger 12. As the plunger 12 moves between the contracted position P1 and the released position P2, the compression spring 16 applies force onto the stirring paddle 14 to maintain the position of the stirring paddle 14 within the syringe barrel 10.

The compression spring 16 disposed within the plunger 12 is preferably in a biased condition before the stirring paddle 14 begins sliding relative to the plunger 12 from the contracted position P1.

The syringe apparatus 1 further includes a needle 18 and a piston 20. The needle 18 is attached to the syringe barrel 10 and the piston 20 is disposed on the plunger 12.

Before injection, one or more compositions to be injected are extracted from composition containers through the needle 18 and drawn into the syringe barrel 10 by the pulling force created by the plunger 12 moving away from the syringe barrel 10. As the compositions are transferred to the syringe apparatus 1 directly through the needle 18, the hygiene condition is well-maintained and guaranteed.

As shown in FIG. 1B, the syringe barrel 10 is, for example, designed as a hollow cylinder or barrel that is used for containing compositions before injection. The syringe barrel 10 has two coaxially positioned openings 101 and 103 opposite to each other. In an embodiment, the opening 101 is preferably funnel-shaped for being easily equipped with the needle 18. In an embodiment, the opening 103 is configured to receive the plunger 12.

The syringe barrel 10 further includes a gripping structure 105 disposed around the opening 103. The gripping structure 105 is designed for providing the user with a holding function when utilizing the syringe apparatus 1. In an embodiment, the gripping structure 105 is designed as an oval-shaped flange surrounding the opening 103 for the user to manipulate the syringe apparatus 1 with fingers.

Figure 2A:
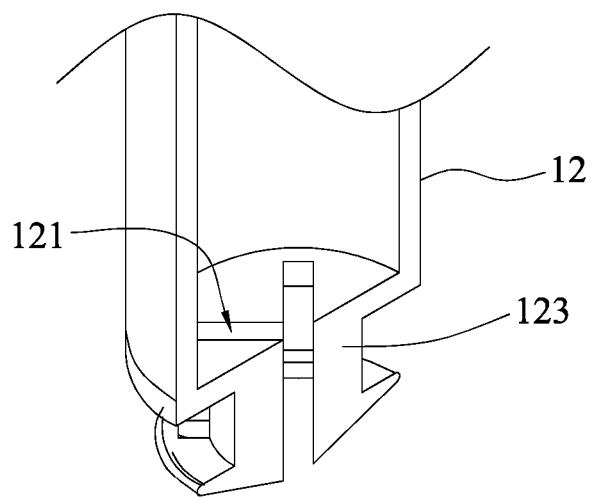
FIG. 2A is a partial enlarged view of the plunger provided in FIG. 1B.

The plunger 12 is disposed within the syringe barrel 10 through the opening 103, and the stirring paddle 14 within the syringe barrel 10 passes through plunger 12. Referring to FIG. 2A, a partial enlarged view of the plunger 12 indicated as 2A in FIG. 1B is provided. The plunger 12 has an opening 121 at the distal end of the plunger 12, such that the stirring paddle 14 couples with and passes through the plunger 12.

Figure 3A:
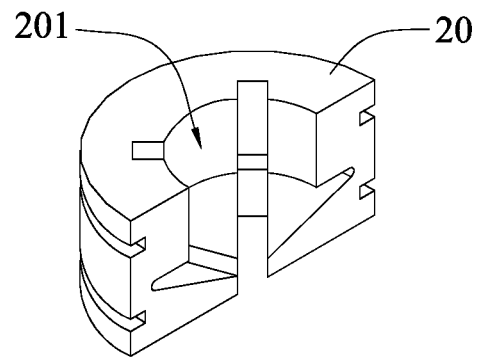
FIG. 3A shows the piston provided in FIG. 1B.
Figure 3B:
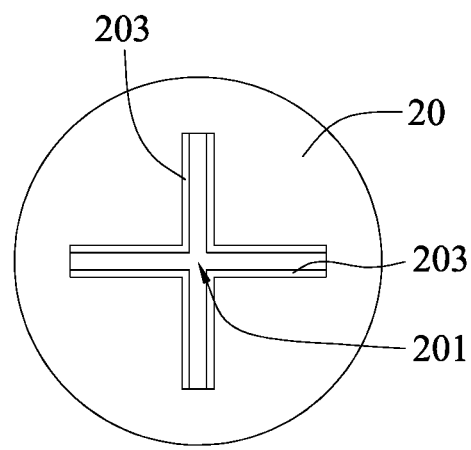
FIG. 3B illustrates a bottom view of the piston provided in FIG. 3A.

As shown in FIG. 2A, the plunger 12 further has a plunger head 123 for engaging the piston 20. Referring to FIG. 3A, the piston 20 in FIG. 1B is shown. The piston 20 is disposed on the plunger 12 and overlapped with the opening 121. The piston 20 has a through hole 201 corresponding to the plunger head 123. In an embodiment, the piston 20 is made of rubber which, for example, serves as a seal to prevent the compositions from leaking through the gap formed between the syringe barrel 10 and the plunger 12. As shown in FIG. 3B which illustrates a bottom view of the piston 20 provided in FIG. 3A, the piston 20 further has a plurality of scrapers 203 disposed around the through hole 201. The scrapers 203 are in contact with the stirring paddle 14 for sealing the gap between the stirring paddle 14 and the piston 20.

The plunger head 123 is, for example, enwrapped by the piston 20. In an embodiment, the opening 121 of the plunger 12 extends from an inner surface of the plunger 12 to an outer surface of the plunger head 123. The shape of the through hole 201 is conformed to the shape of the plunger head 123 and the opening 121.

As shown in FIG. 1B, the plunger 12 further has an end panel 125 which facilitates the user to push the plunger 12 into the syringe barrel 10 or withdraw the plunger 12 out of the syringe barrel 10. It should be appreciated that although the plunger 12 is illustrated by a barrel or a cylinder, other shapes of the plunger are applicable in the present disclosure.

Figure 4A:
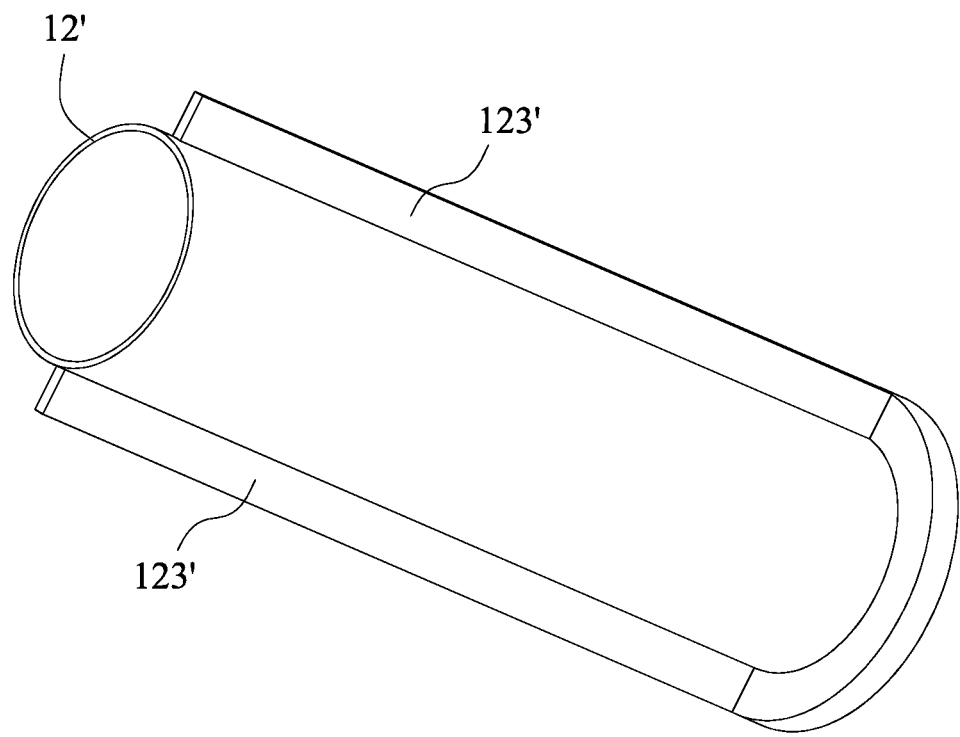
FIG. 4A shows the plunger designed with ribs.
Figure 4B:
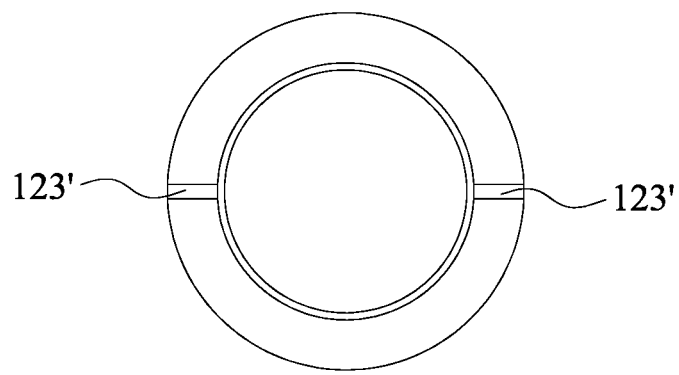
FIG. 4B is a bottom view of the plunger provided in FIG. 4A.

FIG. 4A shows that the plunger 12' may be further designed with ribs 123', and FIG. 4B is a cross-sectional view of the plunger 12' provided in FIG. 4A. As shown in FIGS. 4A and 4B, the plunger 12' has a plurality of ribs 123' longitudinally disposed on the external surface of the plunger 12'. The rib design can reduce the contact area between the plunger 12' and the syringe barrel 10 while maintaining the positioning of the plunger 12' within the syringe barrel 10. Accordingly, the friction resistance generated by the movement of the plunger 12' is lowered, enabling the movement of the plunger 12' easier.

Figure 2B:
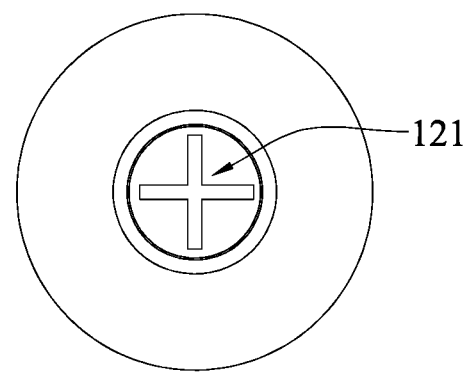
FIG. 2B illustrates a bottom view of the plunger provided in FIG. 1B.
Figure 5A:
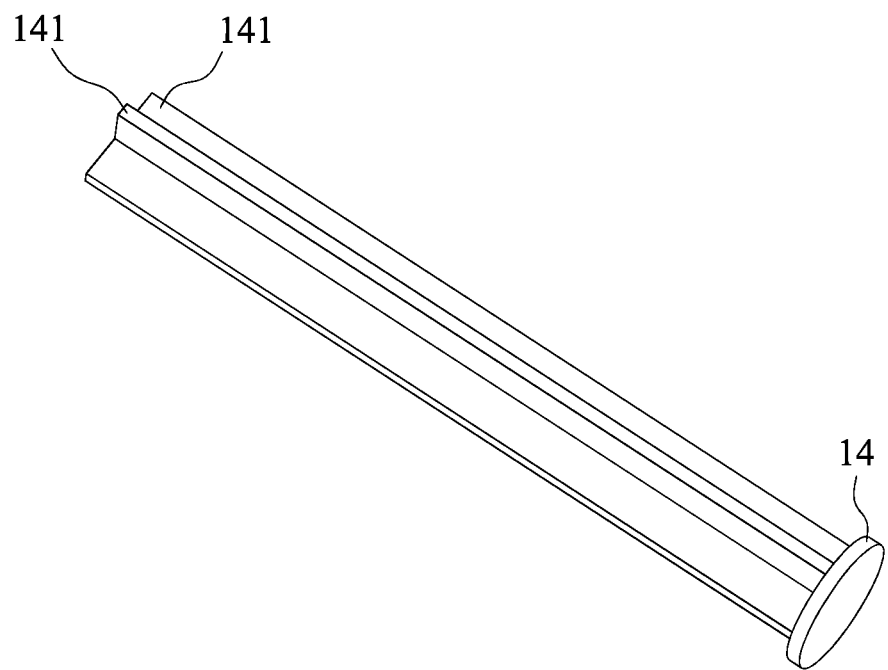
FIG. 5A is a plan view of the stirring paddle provided in FIG. 1B.

Referring back to FIG. 1B, the stirring paddle 14 disposed within the syringe barrel 10 has one end adjacent to the opening 101 and the other end coupled with the plunger 12 through the opening 123. FIG. 5A is a plan view of the stirring paddle 14 provided in FIG. 1B. The stirring paddle 14 is shaped to slidably couple with the plunger 12. For example, the opening 121 of the plunger 12 is designed to have a shape conforming to the cross-sectional shape of the stirring paddle 14. Thus, the stirring paddle 14 remains free to slide within the plunger 12 while the rotation of the stirring paddle 14 relative to the plunger 12 is constrained. For example, the stirring paddle 14 shown in FIG. 5A includes two intersecting blades 141, and the plunger 12 shown in FIG. 2B, which illustrates a bottom view of the plunger 12 in FIG. 1B, has a corresponding cross-shaped opening 121.

Given above arrangement, when the plunger 12 is rotated, the stirring paddle 14 rotates along with the plunger 12, such that the composition within the syringe barrel 10 is stirred by the stirring paddle 14.

Figure 5B:
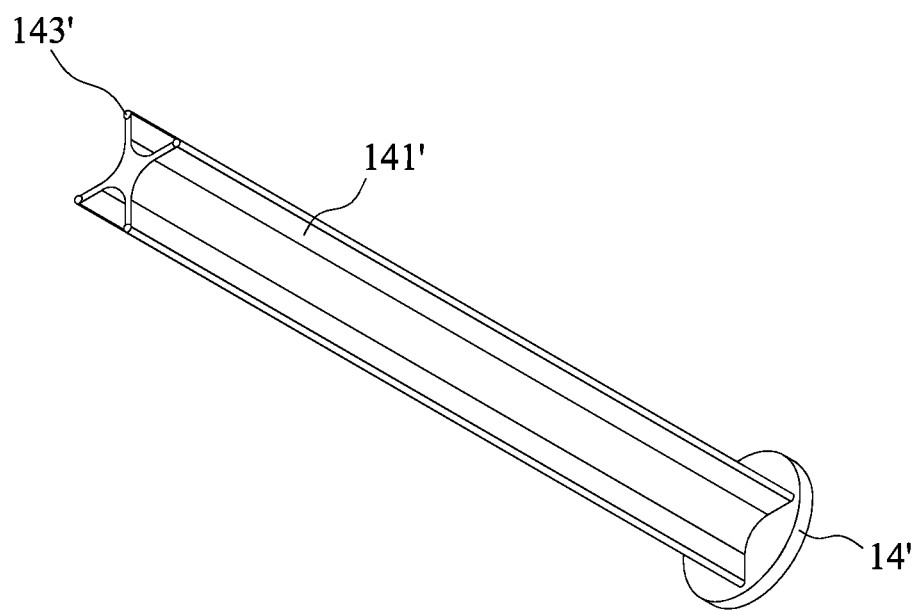
FIG. 5B shows the stirring paddle having a curved cross-sectional shape.
Figure 5C:
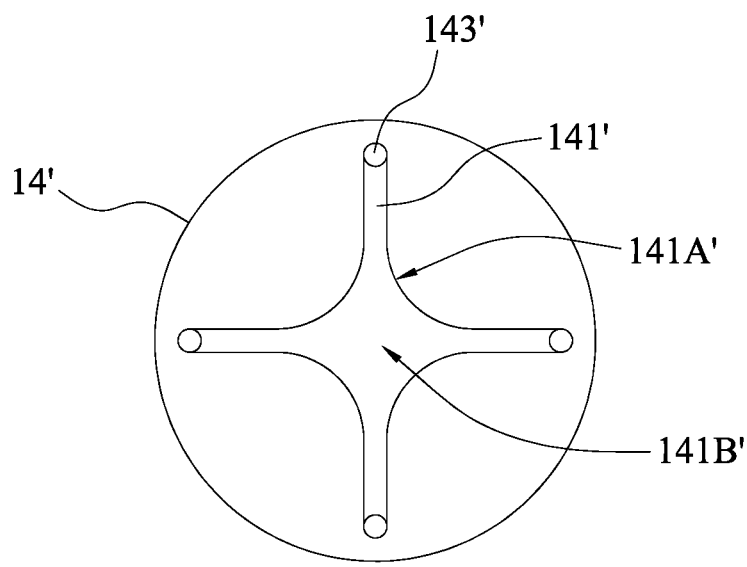
FIG. 5C illustrates a bottom view of the stirring paddle provided in FIG. 5B.

In the situation that the composition contains cells, it is preferable to thoroughly stir the composition while preserving the cells without damaging them. As shown in FIGS. 5B and 5C, the cross-sectional shape formed by the two intersecting blades 141' of the stirring paddle 14' has a plurality of curves 141A'. As such, when the stirring paddle 14' rotates, the curves 141A' push the composition to flow as vortex, enhancing the uniformity of the composition.

Figure 5D:
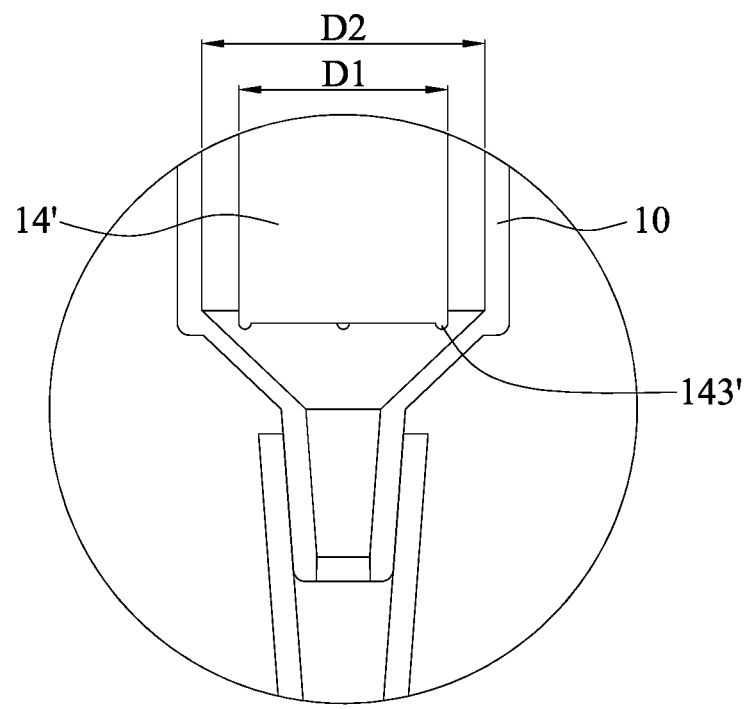
FIG. 5D shows the stirring paddle of FIG. 5B within the syringe barrel.

In an embodiment, the stirring paddle 14' further has a plurality of protrusions 143' on the end surface 141B' of the stirring paddle 14'. As illustrated in FIG. 5D which shows the stirring paddle 14' of FIG. 5B within the syringe barrel 10, the protrusions 143' preferably have circular surfaces to reduce the contact between the stirring paddle 14' and the syringe barrel 10. Moreover, the stirring paddle 14' has an outer diameter D1 smaller than an inner diameter D2 of the syringe barrel 10, such that the contact between the stirring paddle 14' and the syringe barrel 10 is minimized, preventing the cells from being damaged during the stirring process.

In an embodiment, at least one of the blades of the stirring paddle has through holes or a chipping edge for improving the stirring effect. The through holes and the chipping edge reduce the resistance from the compositions that the stirring paddle 14 encounters when rotating inside the syringe barrel 10. For example, the stirring paddle having through holes of different shapes is shown in FIGS. 6A and 6B, and the stirring paddle having different chipping edges is shown in FIGS. 7A and 7B. In an embodiment, the through holes are round holes or square holes, and it should be appreciated that other shapes of the through holes are applicable in the present disclosure. In an embodiment, the chipping edges may be saw-tooth shaped or fence-shaped, and it should also be appreciated that other shapes of the chipping edges are applicable in the present disclosure.

In an embodiment, the syringe apparatus further includes a needle length-control device having a connecting base and a protection cap, wherein the connecting base is attached to the syringe barrel, the protection cap is movably mounted with the connecting base and has a mouth end surrounding the needle. The protection cap moves relative to the connecting base for concealing or exposing at least a portion of the needle.

In an embodiment, the syringe apparatus further includes a dosage-control device having a connecting base and a plunger-restraint component, where the connecting base is attached to the syringe barrel, the plunger-restraint component is movably mounted with the connecting base and partially receives the plunger, and the plunger-restraint component is capable of stopping the plunger when the plunger reaches the plunger-restraint component. The movement of the plunger-restraint component relative to the connecting base controls a pre-determined distance of the plunger moving relative to the syringe barrel, such that a pre-setup dosage corresponding to the pre-determined distance is controlled.

Figure 8A:
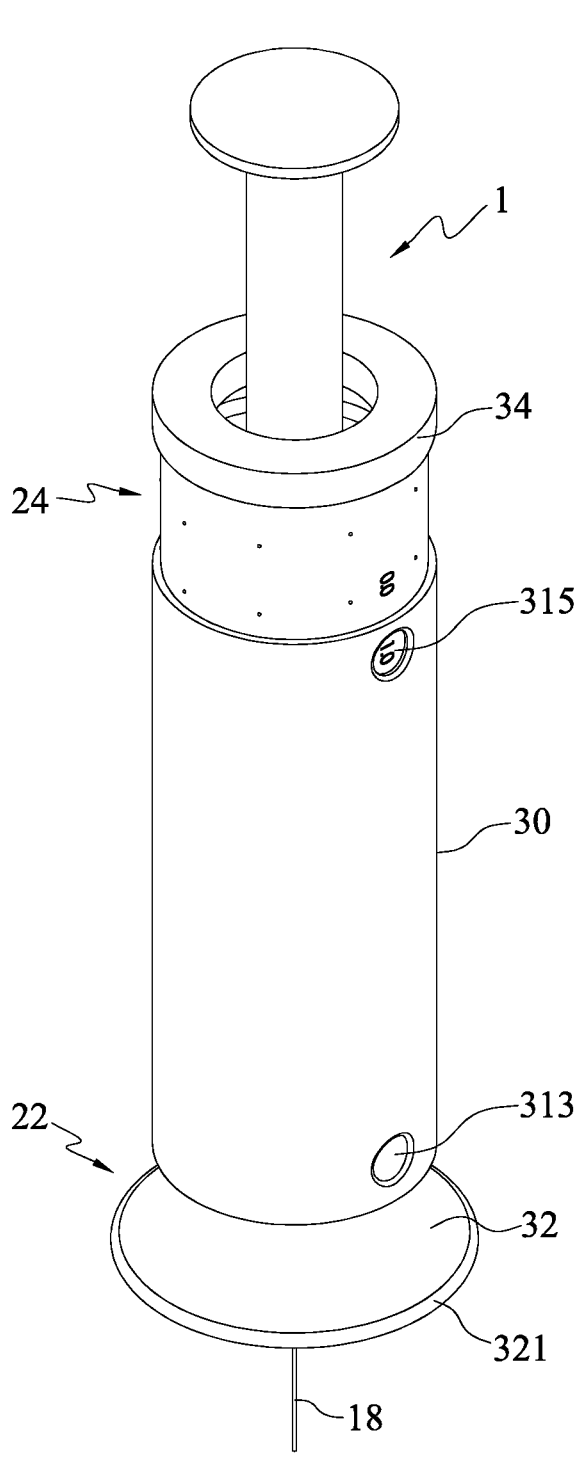
FIG. 8A is a perspective view of the syringe apparatus having a needle length-control device and a dosage-control device.
Figure 8B:
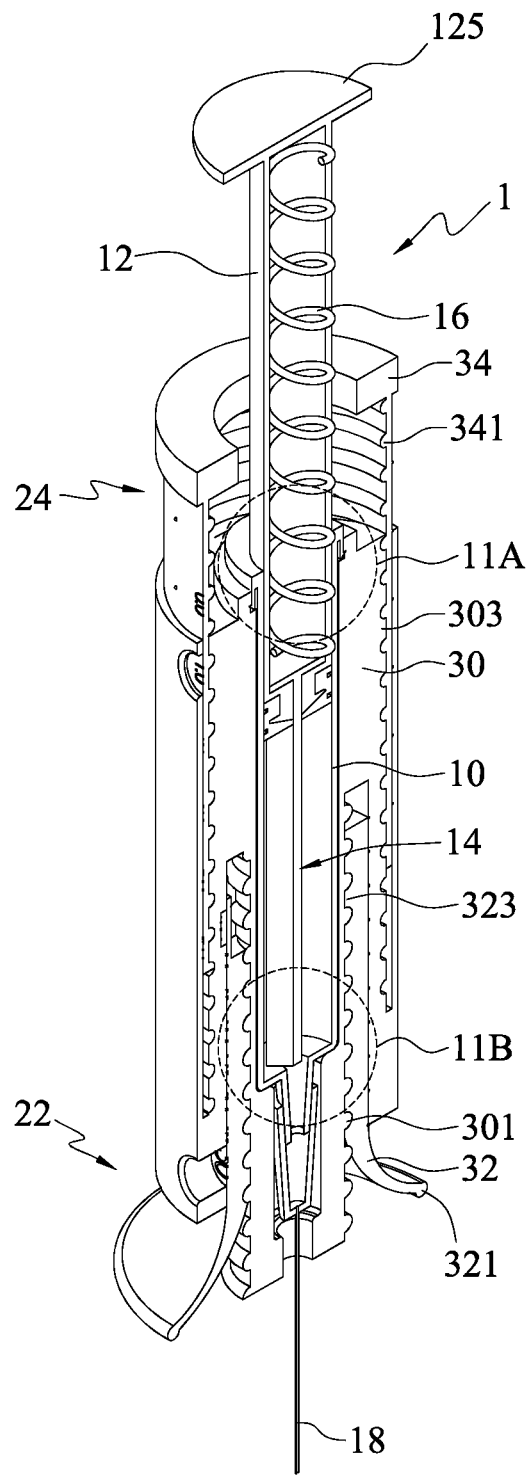
FIG. 8B is a cross-sectional perspective view of the syringe apparatus provided in FIG. 8A.

FIG. 8A is a perspective view of the syringe apparatus 1 having a needle length-control device 22 and a dosage-control device 24. FIG. 8B is a cross-sectional perspective view of the syringe apparatus 1 in FIG. 8A. For the reason that both the needle length-control device 22 and the dosage-control device 24 are assembled with the syringe barrel 10 of the syringe apparatus 1, both the needle length-control device 22 and the dosage-control device 24 shown in FIGS. 8A and 8B are combined as one complete module. However, this should not be construed to limit the scope of the present disclosure as the needle length-control device 22 and the dosage-control device 24 function independently, and can be employed individually or collaboratively with the syringe apparatus 1.

Figure 10A:
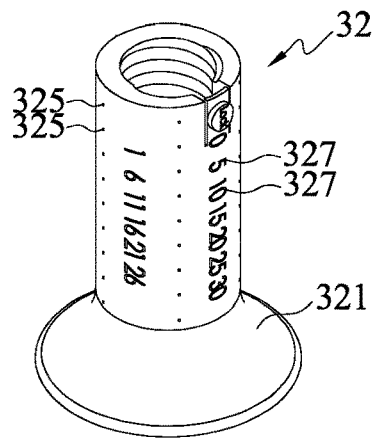
FIG. 10A is a perspective view of the protection cap in FIG. 8A.
Figure 10A:
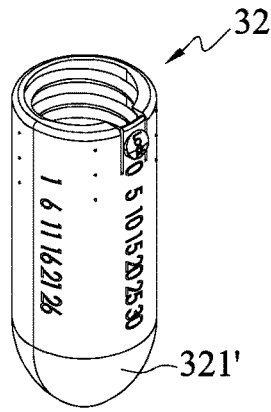

As shown in FIG. 8A, the needle length-control device 22 and the dosage-control device 24 have a connecting base 30 attached to the syringe barrel 10. The needle length-control device 22 further has a protection cap 32 movably mounted with the connecting base 30. In one embodiment, the protection cap 32 may have a flared shield 321 surrounding the needle 18. In another embodiment, the protection cap 32 may have a round convex shield 321' as shown in FIG. 10A'. Accordingly, when the protection cap 32 moves relative to the connecting base 30, the protection cap 32 conceals or exposes at least a portion of the needle 18.

The dosage-control device 24 further has a plunger-restraint component 34 movably mounted with the connecting base 30 and partially receiving the plunger 12. The plunger-restraint component 34 is capable of stopping the plunger 12 when the plunger 12 reaches the plunger-restraint component 34 due to the size of the end panel 125. The movement of the plunger-restraint component 34 relative to the connecting base 30 controls a pre-determined distance of the plunger 12 moving relative to the syringe barrel 10, such that a pre-setup dosage corresponding to the pre-determined distance is controlled.

As shown in FIG. 8A, the connecting base 30 further has two indicating windows 313 and 315 for providing the user with the access to read the adjustments of the protection cap 32 and the plunger-restraint component 34, respectively.

Preferably, the protection cap 32 and the plunger-restraint component 34 are rotatable around the connecting base 30, and are movable along an axial length of the connecting base 30 when rotating.

As shown in FIG. 8B, the connecting base 30 has a screw thread 301, and the protection cap 32 has a screw thread 323 engaging the screw thread 301. As the protection cap 32 rotates relative to the connecting base 30, the protection cap 32 moves along the axial length of the connecting base 30. The connecting base 30 further has a screw thread 303, and the plunger-restraint component 34 has a screw thread 341 engaging the screw thread 303. As the plunger-restraint component 34 rotates relative to the connecting base 30, the plunger-restraint component 34 moves along the axial length of the connecting base 30. The protection cap 32 and the plunger-restraint component 34 are able to rotate into the connecting base 30 or in the direction out away from the connecting base 30.

Figure 9:
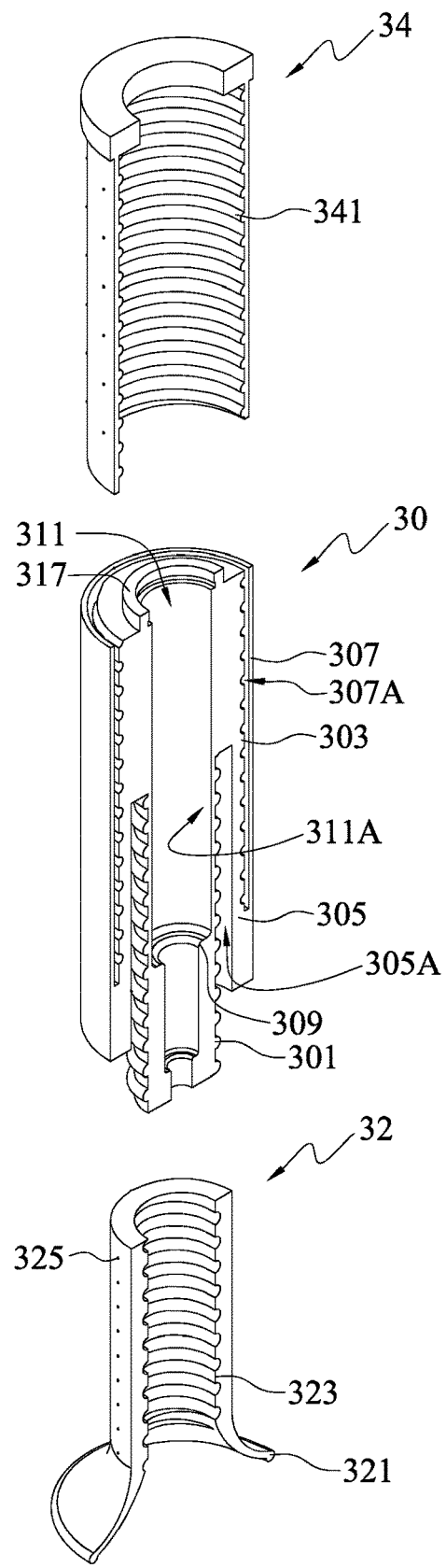
FIG. 9 is an exploded perspective view of the needle length-control device and the dosage-control device in FIG. 8B.

FIG. 9 is an exploded perspective view of the needle length-control device 22 and the dosage-control device 24 shown in FIG. 8B. The connecting base 30 further has an enclosing sleeve 305 forming a receiving groove 305A within the connecting base 30. The receiving groove 305A extends along the axial length of the connecting base 30, and the protection cap 32 is inserted into the receiving groove 305A and surrounded by the enclosing sleeve 305. The screw thread 301 is disposed opposite to the enclosing sleeve 305.

The connecting base 30 further has another enclosing sleeve 307 forming a receiving groove 307A within the connecting base 30. The receiving groove 307A extends along the axial length of the connecting base 30, and the plunger-restraint component 34 is inserted into the receiving groove 307A and surrounded by the enclosing sleeve 307. The screw thread 303 is disposed opposite to the enclosing sleeve 307. As shown in FIG. 9, the receiving grooves 305A and 307A are disposed in parallel and partially overlapped. However, as the needle length-control device 22 and the dosage-control device 24 are used separately, this overlapping is not necessary. Persons skilled in the art should appreciate that the overlapping and the extending lengths of the receiving grooves 305A and 307A are designed based on the dimensions of the syringe apparatus 1.

The connecting base 30 further has a holding edge 309 and a passageway 311. The syringe barrel 10 may be disposed within the connecting base 30 through the passageway 311. The holding edge 309 is located on an internal surface 311A of the connecting base 30 and narrows the passageway 311, such that the syringe barrel 10 can be stopped by the holding edge 309 and positioned on the connecting base 30. When the syringe barrel 10 is positioned on the connecting base 30, the holding edge 309 surrounds the opening 101 of the syringe barrel 10.

As shown in FIG. 9, the protection cap 32 has the screw thread 323 on the inner surface. The protection cap 32 is screwed into the receiving groove 305A of the connecting base 30 by the engagement of the screw thread 323 and the screw thread 301. In an embodiment, the protection cap 32 further has at least one bump 325 on the external surface thereof for temporary locking the protection cap 32 on the connecting base 30 by embedding into a concave (not shown) on the internal surface of the enclosing sleeve 305 along the moving path of the protection cap 32.

Referring to FIG. 10A, a perspective view of the protection cap 32 shown in FIG. 8A is provided. As shown in FIG. 10A, a plurality of bumps 325 are disposed on the external surface of the protection cap 32 with spacing. In an embodiment, the plurality of bumps 325 with spacing provide the user a feedback to tell a certain increment of the exposed needle length. The protection cap 32 further has a plurality of markings 327 corresponding to different needle lengths that are available for injection. For example, as the protection cap 32 is rotated into the connecting base 30, the marking 327 of higher number is displayed in the indicating window 313 (shown in FIG. 8A). As such, a longer needle length is provided for injection. Otherwise, a shorter needle length is anticipated as the protection cap 32 is rotated out of the connecting base 30. In one embodiment, the markings 327 may be numerals that appear upright along the axial direction of the protection cap 32 in the indicating window 313 for users to easily recognize the needle side of the syringe apparatus 1, thereby avoiding accidental injury of the users by the needle 18.

As depicted in FIG. 9, the plunger-restraint component 34 has the screw thread 341 on the inner surface. The plunger-restraint component 34 is screwed into the receiving groove 307A of the connecting base 30 by the engagement of the screw thread 341 and the screw thread 303. In an embodiment, the plunger-restraint component 34 further has at least one bump 343 on the external surface thereof for temporary locking the plunger-restraint component 34 on the connecting base 30 by embedding into a concave (not shown) on the internal surface of the enclosing sleeve 307 along the moving path of the plunger-restraint component 34.

Figure 10B:
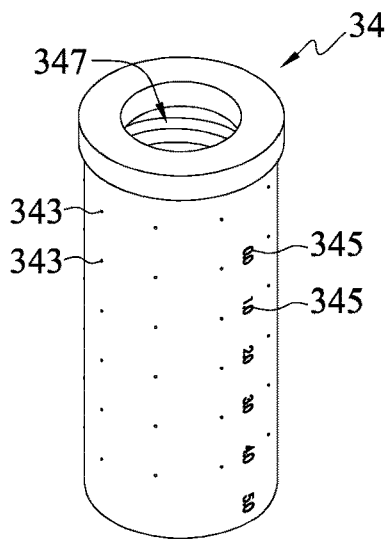
FIG. 10B is a perspective view of the plunger-restraint component in FIG. 8A.

Referring to FIG. 10B, a perspective view of the plunger-restraint component 34 shown in FIG. 8A is provided. As shown in FIG. 10B, a plurality of bumps 343 are disposed on the external surface of the plunger-restraint component 34 with spacing. In an embodiment, the plurality of bumps 343 with spacing provide the user a feedback to tell a certain increment of a pre-setup dosage. The plunger-restraint component 34 further has a plurality of markings 345 corresponding to different dosages that are available for injection. The markings 345 are sequentially displayed in the indicating window 315 during the moving of the plunger-restraint component 34.

The plunger-restraint component 34 has a top opening 347 designed to be smaller than the end panel 125 of the plunger 12 (shown in FIGS. 8B and 10B), so that the plunger-restraint component 34 is able to stop the plunger 12 as the end panel 125 reaches the top opening 347. As the plunger-restraint component 34 is rotated to move deeper into the connecting base 30, a longer spacing distance between the end panel 125 and the plunger-restraint component 34 is available, such that the pre-determined distance for the plunger-restraint component 34 is set, and the pre-setup dosage is controlled.

Figure 11A:
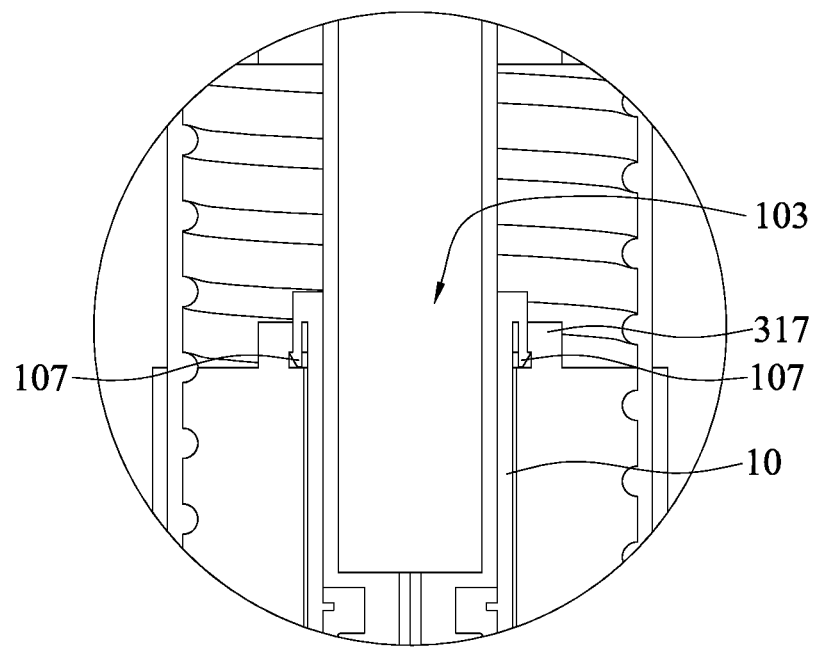
FIG. 11A is a first partial enlarged cross-sectional view of the syringe barrel and the connecting base in FIG. 8B.
Figure 11B:
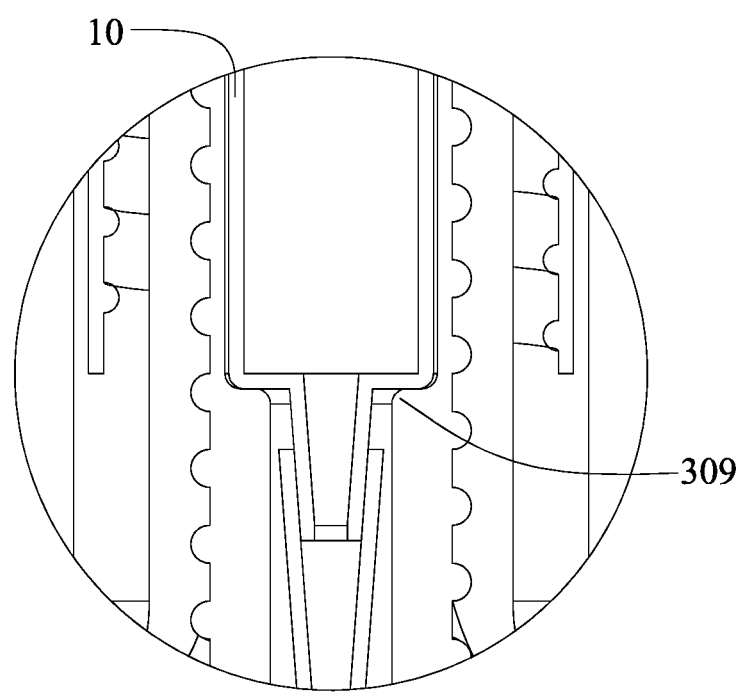
FIG. 11B is a second partial enlarged cross-sectional view of the syringe barrel and the connecting base in FIG. 8B.

FIG. 11A is a first partial enlarged cross-sectional view of the syringe barrel 10 and the connecting base 30 indicated as 11A in FIG. 8B. FIG. 11B is a second partial enlarged cross-sectional view of the syringe barrel 10 and the connecting base 30 indicated as 11B in FIG. 8B.

For fastening the syringe barrel 10 on the connecting base 30, the connecting base 30 further has a locking rib 317 disposed on the top surface of the connecting base 30 (referring also to FIG. 9). The locking rib 317 extends around the entrance of the passageway 311 and preferably encircles the entrance. In an embodiment, the syringe barrel 10 further has a pair of hooks 107 adjacent the opening 103 and pointing downwardly. As the syringe barrel 10 is inserted into the passageway 311 of the connecting base 30, one end of the syringe barrel 10 is positioned against the holding edge 309, and the hooks 107 on the other end of the syringe barrel 10 are embedded in the locking rib 317, such that the syringe barrel 10 is fastened.

Figure 12:
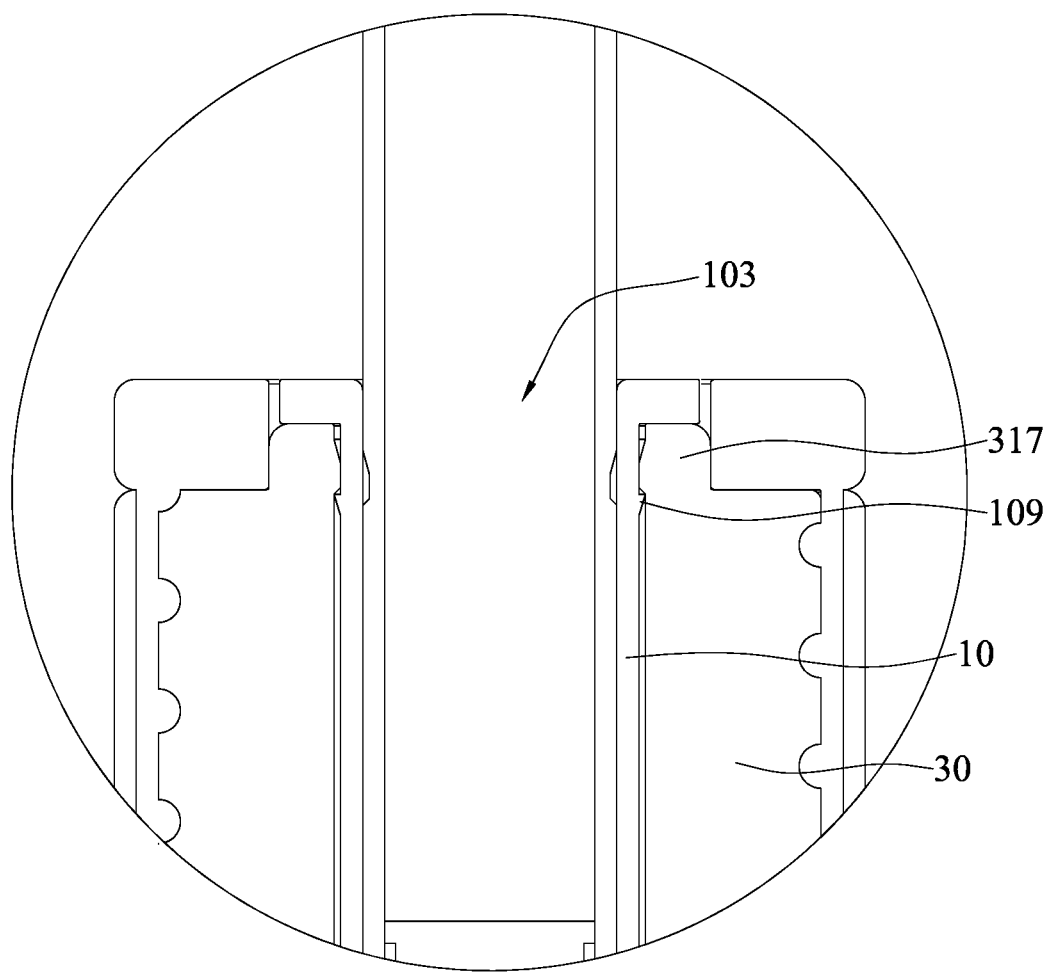
FIG. 12 shows an alternative engagement between the syringe barrel and the connecting base provided in FIG. 11A.

FIG. 12 shows an embodiment providing an alternative engagement between the syringe barrel 10 and the connecting base 30 in FIG. 11A. The syringe barrel 10 further has a locking ring 109 on an external surface of the syringe barrel 10 and adjacent to the opening 103. The locking ring 109 engages the connecting base 30 by embedding in the locking rib 317, such that the syringe barrel 10 will not be pushed back during the injection.

The syringe apparatus disclosed in an embodiment includes a stirring paddle for stirring the composition inside the syringe apparatus before injection. The composition to be injected is directly loaded to the syringe apparatus by being extracted through the needle of the syringe apparatus from the composition containers. The composition is then stirred inside the syringe apparatus and ready to be delivered without removing the stirring paddle from the syringe apparatus. The whole process avoids the potential risk of contaminating the compositions during the conventional way for stirring the composition before placing the composition into the syringe apparatus.

In addition, the syringe apparatus includes, for example, a compression spring that presses the stirring paddle within the syringe apparatus, such that when the plunger is pulled by the user to draw the composition into the syringe apparatus, the stirring paddle under the pressure of the compression spring remains its position inside the syringe apparatus without being pulled away with the plunger, ensuring that the stirring paddle stirs the composition with its full function.

Furthermore, higher precision of the injection and a safer use of the needle are achievable as the syringe apparatus is equipped with a needle length-control device and a dosage-control device disclosed above in the embodiment. Accordingly, the user can preset the dosage and the needle length through the devices based upon a medical prescription, thereby eliminating the human errors due to the misjudgment of the users.

Figure 13:
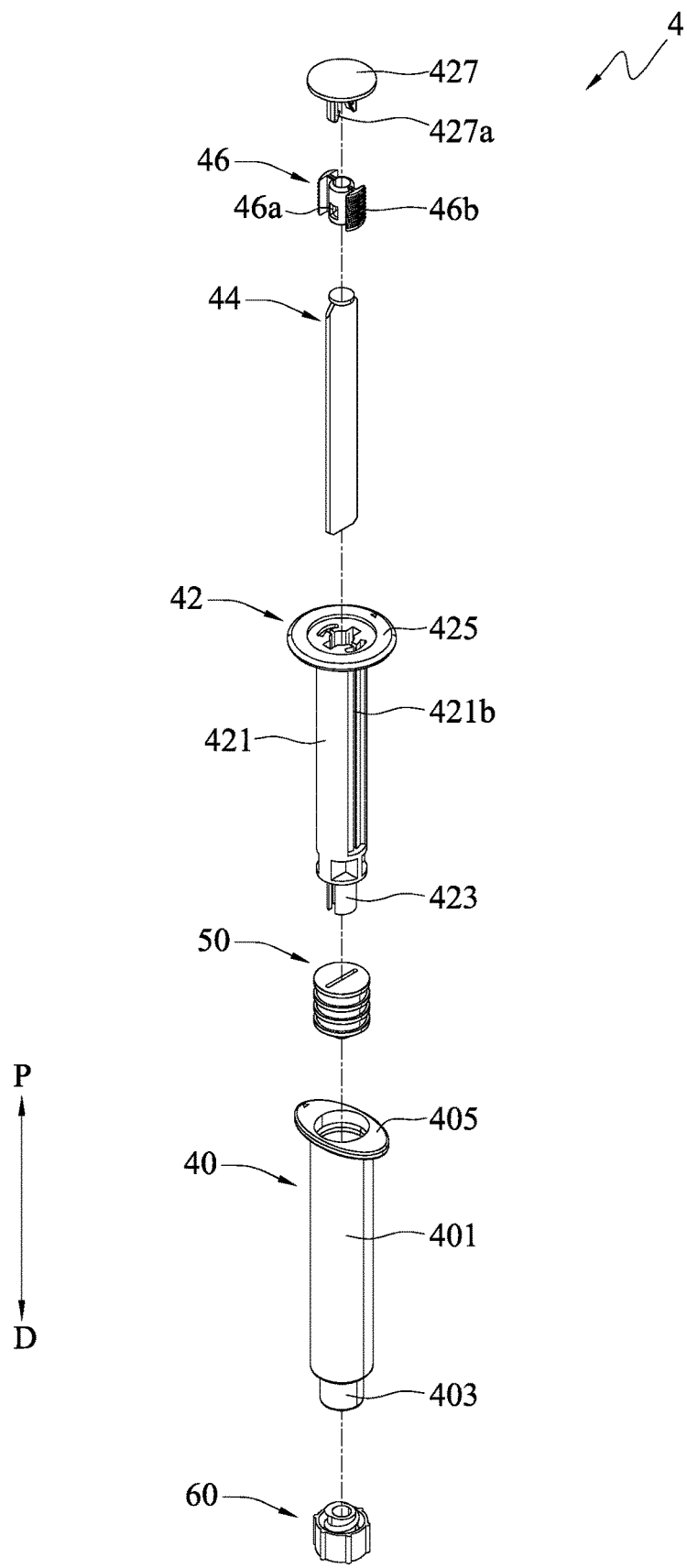
FIG. 13 is an exploded perspective view of the syringe apparatus for stirring and delivering a single or multi-components composition according to an embodiment of the present disclosure.

In another embodiment, FIG. 13 shows an exploded perspective view of the syringe apparatus 4 for stirring and delivering single or multi-components composition according to an embodiment of the present disclosure. The terms "proximal," "backward" or "withdrawing" refer generally to an axial direction in the direction "P." The terms "distal," "frontward" or "pressing" refer generally to an axial direction in the direction "D."

As shown in FIG. 13, the syringe apparatus 4 includes a syringe barrel 40, a plunger 42 detachably disposed within the syringe barrel 40, a stirring paddle 44 detachably disposed within the plunger 42, a connecting member 46 for connecting the stirring paddle 44 and the plunger 42, and a piston 50 for connecting with the plunger 12, and a lid 60 for covering the syringe barrel 40. In one embodiment, the connecting member 46 can be an actuable mechanism 46.

The syringe barrel 40 has a barrel body 401 with a cylinder or a barrel shape, a barrel tip 403 at its distal end for being connected with the lid 60 or a needle 18 as shown in FIGS. 1A and 1B), and a gripping structure 405 with a circular or an oval shape at its proximal end.

In one embodiment, the barrel tip 403 and the lid can be Luer taper that prevents the syringe barrel 40 from leakage.

The plunger 42 has a plunger body 421 for being received in the barrel body 401, a plunger head 423 at its distal end for being enwrapped by the piston 50, an end panel 425 at its proximal end for protruding from the gripping structure 405 as the plunger body 421 is inserted into the barrel body 401, and a corresponding actuable mechanism 427 disposed on the end panel 425. Also, the plunger head 423 and the piston 50 have openings corresponding to each other, such that the stirring paddle 44 can pass through the openings of the plunger 423 and the piston 50, as shown in FIGS. 2A to 3B. Moreover, the plunger 42 can move in the barrel body 401 in an axial direction of the syringe barrel 40, i.e., the directions P or D. By withdrawing or pressing the plunger 42, the single or multi-components composition can flow into or flow out of the syringe barrel 40. In addition, the plunger 42 further includes a guiding element 421b (e.g., a track) on the plunger body 421, and the corresponding actuable mechanism 427 includes a corresponding locking part 427a (e.g., a pair of hooks) to engage the actuable mechanism 46 for locking.

The stirring paddle 44 can be inserted into the plunger body 421, pass through the openings of the plunger head 423 and the piston 50, and then protrude into the barrel body 401. Also, as shown in FIGS. 5A to 5D, the stirring paddle 44 can have one or more blades or intersecting blades with a curved interface, or have a protrusion toward a distal end of the stirring paddle 44 on each blade at its distal end. Moreover, as shown in FIGS. 6A to 7B, the blade of the stirring paddle can further have through holes penetrating the blade, such that the single or multi-components composition can flow through the through holes when the stirring paddle 44 is stirred, or have chipping edges for facilitating the uniform of the stirring. In addition, the stirring paddle 44 can be connected with the actuable mechanism 46 at the proximal end of the stirring paddle 44.

In one embodiment, the stirring paddle 44 is one single blade with a flat shape. In another embodiment, the stirring paddle 44 may have curved corners at the distal end thereof.

In one embodiment, the actuable mechanism 46 is connected with the proximal end of the stirring paddle 44. The actuable mechanism 46 can further have a locking part 46a (e.g., a pair of recesses) and a sliding element 46b (e.g., a sliding block). As the sliding element 46b is in slidable contact with the guiding element 421b for the actuable mechanism 46 to move backward or frontward on the guiding element 421b, the stirring paddle 44 can move in the plunger body 421 relative to the plunger 42 in the direction P and D. In other words, the plunger 42 is movable relative to the stirring paddle 44 along the axial direction. Moreover, as the locking part 46a (e.g., a pair of recesses) engaging the corresponding locking part 427a (e.g., a pair of hooks), the stirring paddle 44 is locked by the locking part 46a without movement relative to the plunger 42. Therefore, upon the locking part 46a engaging the corresponding locking part 427a, the stirring paddle 44 would not protrude from the plunger 42 into the barrel body 401, such that the syringe apparatus 4 cannot be used anymore.

FIGS. 14A to 14D are four states of the use of the syringe apparatus 4 according to an embodiment of the present disclosure.

Figure 14A:
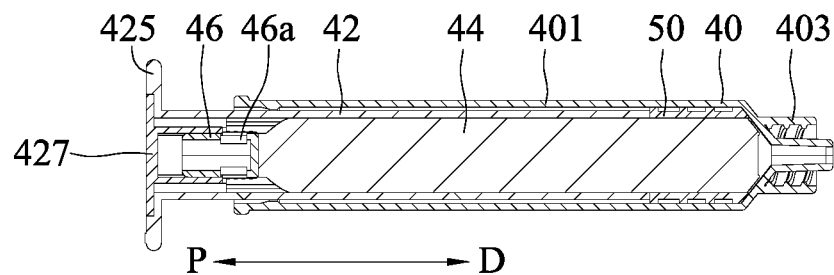
FIGS. 14A to 14D show four states of use of the syringe apparatus of FIG. 13.

As shown in FIG. 14A, at an initial state, the plunger 42 enwrapped with the piston 50 is inserted in the barrel body 401 of the syringe barrel 40 to the distal end of the barrel body 401 such that there exists no air between the piston 50 and the syringe tip 403. The stirring paddle 44 is also inserted in the plunger body 421 to the distal end of the plunger body 421, and the actuable mechanism 46 disposed on the proximal end of the stirring paddle 44 is free from engaging the corresponding actuable mechanism 427 disposed on the end panel 425.

Figure 14B:
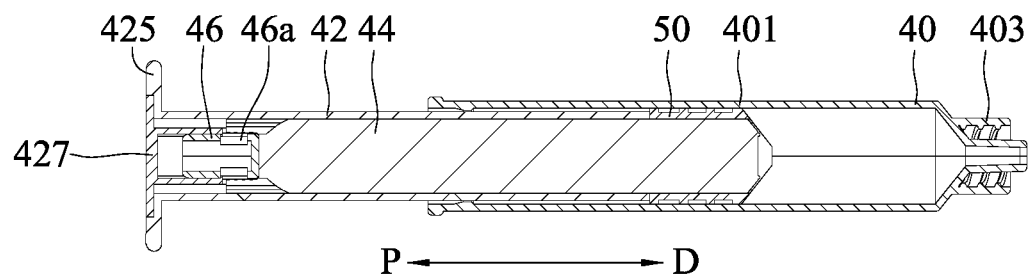

Next, as shown in FIG. 14B, when the plunger 42 is withdrawn to draw the single or multi-components composition, and the stirring paddle 44 is movable with the plunger 42.

Figure 14C:
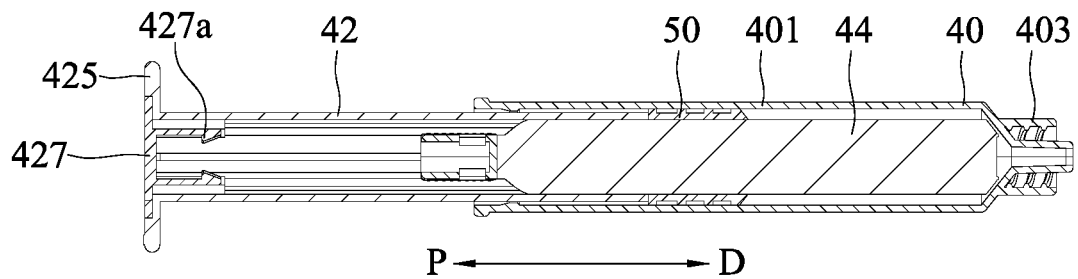

Further, as shown in FIG. 14C, there exist a specific amount of the single or multi-components composition in the syringe body 401. An user can push the stirring paddle 44 to protrude the stirring paddle 44 from the plunger body 421 into the syringe body 401, and then rotate the plunger 42 to drive the stirring paddle 44 to rotate together, so as to stirring the single or multi-component composition in the syringe body 401.

Figure 14D:
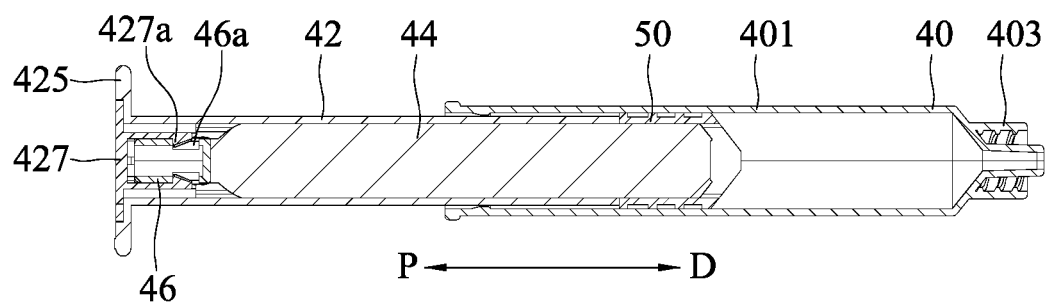

After stirring, as shown in FIG. 14D, the stirring paddle 44 can be withdrawn backward until the actuable mechanism 46 engages the corresponding actuable mechanism 427. Alternatively, the stirring paddle 44 can be pulled backward after the plunger 42 is pressed to inject the single or multi-component composition out from the syringe barrel 40. Upon the actuable mechanism 46 disposed at the proximal end of the stirring paddle 44 engages the corresponding actuable mechanism 427 disposed at the end panel 425, the stirring paddle 44 would be no longer movable relative to the plunger 42, and thus the syringe apparatus 4 cannot be used any more as a disposable syringe apparatus. As such, mutual infection can be avoided.

In other embodiments, the syringe apparatus 4 illustrated in FIG. 13 can also be attached with a plunger-restraint component, a connecting base and a protection cap as shown in FIGS. 8A to 12.

The above-described descriptions of the detailed embodiments are only to illustrate the implementation according to the present disclosure, and it is not to limit the scope of the present disclosure. Accordingly, all modifications and variations completed by those with ordinary skill in the art should fall within the scope of the present disclosure defined by the appended claims.

What is claimed is:

1. A syringe apparatus comprising:
a syringe barrel having an axial direction;
a plunger detachably disposed within the syringe barrel and being movable within the syringe barrel along the axial direction of the syringe barrel, the plunger including:
a plunger body received in the syringe barrel;
an end panel disposed at a proximal end of the plunger and protruding from the syringe barrel;
a guiding element disposed on the plunger body; and
a corresponding actuable mechanism disposed on the end panel and having a corresponding locking part;
a stirring paddle detachably disposed within the plunger body with the plunger being movable relative to the stirring paddle along the axial direction of the syringe barrel; and
a connecting member detachably disposed within the plunger body and detachably connected between a proximal end of the stirring paddle and the end panel of the plunger,
wherein the connecting member is an actuable mechanism having a locking part and is disposed on the proximal end of the stirring paddle,
wherein the stirring paddle is configured to move along the axial direction of the syringe barrel by the connecting member in slidable contact with the guiding element, and the stirring paddle is free of moving relative to the plunger when the locking part of the actuable mechanism engages the corresponding locking part of the corresponding actuable mechanism,
wherein the plunger includes a plunger head with an opening, the syringe apparatus further comprises a piston detachably engaging the plunger head, and the piston includes a through hole corresponding to and communicating with the opening for the stirring paddle to project therethrough, and
wherein the piston includes a plurality of scrapers disposed around the through hole, and the scrapers are in contact with the stirring paddle and configured to seal a gap between the stirring paddle and the piston.

2. The syringe apparatus of claim 1, further comprising a needle detachably disposed on a distal end of the syringe barrel.

3. The syringe apparatus of claim 2, further comprising a needle length-control device having a connecting base and a protection cap, wherein the connecting base is attached to the syringe barrel, the protection cap is movably mounted with the connecting base and has a mouth end surrounding the needle, and the protection cap is configured to move relative to the connecting base for concealing or exposing at least a portion of the needle.

4. The syringe apparatus of claim 3, wherein the protection cap is rotatable around the connecting base and movable along an axial length of the connecting base.

5. The syringe apparatus of claim 4, wherein the connecting base comprises a first screw thread, and the protection cap comprises a second screw thread engaging the first screw thread.

6. The syringe apparatus of claim 3, wherein the connecting base comprises:
an enclosing sleeve having a receiving groove in the connecting base, wherein the receiving groove extends along the axial length of the connecting base, and the protection cap is inserted into the receiving groove and surrounded by the enclosing sleeve;
at least one concave formed on an internal surface of the enclosing sleeve along a moving path of the protection cap, wherein the protection cap has at least one bump disposed on an external surface of the protection cap corresponding to the at least one concave;
a passageway formed through the connecting base and configured to receive the syringe barrel; and
a holding edge formed on an internal surface of the connecting base and configured to narrow the passageway for positioning the syringe barrel in the connecting base.

7. The syringe apparatus of claim 1, further comprising:
a dosage-control device having a connecting base and a plunger-restraint component, wherein the connecting base is attached to the syringe barrel, the plunger-restraint component is movably mounted with the connecting base and partially receiving the plunger, and the plunger-restraint component is configured to stop the plunger when the plunger reaches the plunger-restraint component, with one movement of the plunger-restraint component relative to the connecting base controlling a pre-determined distance of the plunger moving relative to the syringe barrel, such that a pre-setup dosage corresponding to the pre-determined distance is controlled.

8. The syringe apparatus of claim 7, wherein the plunger-restraint component is rotatable around the connecting base and movable along an axial length of the connecting base, and wherein the connecting base comprises a first screw thread, and the plunger-restraint component comprises a second screw thread engaging the first screw thread.

9. The syringe apparatus of claim 7, wherein the connecting base comprises:
an enclosing sleeve having a receiving groove in the connecting base, wherein the receiving groove extends along the axial length of the connecting base, and the plunger-restraint component is inserted into the receiving groove and surrounded by the enclosing sleeve;
at least one concave formed on an internal surface of the enclosing sleeve along a moving path of the plunger-restraint component, wherein the plunger-restraint component has at least one bump on an external surface of the plunger-restraint component corresponding to the at least one concave; and
a passageway formed through the connecting base and configured to receive the syringe barrel; and
a holding edge formed on an internal surface of the connecting base and configured to narrow the passageway for positioning the syringe barrel in the connecting base.

10. The syringe apparatus of claim 9, wherein the syringe barrel further comprises a pair of hooks at a proximal end of the syringe barrel or a locking ring on an external surface of the syringe barrel at the proximal end of the syringe barrel to engage the connecting base.

11. The syringe apparatus of claim 7, wherein the plunger-restraint component has a top opening, and the end panel is disposed outside the plunger-restraint component and greater in diameter than the top opening.

12. The syringe apparatus of claim 1, wherein the stirring paddle has a cross-sectional shape conforming to the opening and the through hole.

13. The syringe apparatus of claim 1, wherein the stirring paddle has an outer diameter smaller than an inner diameter of the syringe barrel, and the stirring paddle comprises a plurality of protrusions on an end surface at a distal end of the stirring paddle.

14. The syringe apparatus of claim 1, wherein the stirring paddle comprises one or more blades.

15. The syringe apparatus of claim 14, wherein the blades have a plurality of curves adjacent to an intersecting point and have a plurality of through holes or a chipping edge.

16. The syringe apparatus of claim 1, wherein the plunger further comprises a plurality of ribs longitudinally disposed on an external surface of the plunger, and the syringe barrel further comprises a gripping structure having a circular shape or an oval shape.

\* \* \* \* \*